(12) United States Patent
Ostroot

(10) Patent No.: US 8,043,258 B2
(45) Date of Patent: Oct. 25, 2011

(54) FLOW-INFLATED DIFFUSION THERAPEUTIC DELIVERY

(75) Inventor: Tim Ostroot, Cokato, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1169 days.

(21) Appl. No.: 11/337,495

(22) Filed: Jan. 24, 2006

(65) Prior Publication Data
US 2007/0173785 A1     Jul. 26, 2007

(51) Int. Cl.
*A61M 31/00* (2006.01)
*A61M 37/00* (2006.01)

(52) U.S. Cl. .................................... 604/103.01

(58) Field of Classification Search ............ 604/103.01, 604/102.02–102.03, 96.01, 509, 98.01, 103.06, 604/103.08; 606/192; 623/1.27, 1.42
See application file for complete search history.

(56) References Cited

U.S. PATENT DOCUMENTS

| | | | | |
|---|---|---|---|---|
| 4,531,936 | A * | 7/1985 | Gordon | 604/500 |
| 5,213,576 | A * | 5/1993 | Abiuso et al. | 604/103.01 |
| 5,378,237 | A * | 1/1995 | Boussignac et al. | 604/103.01 |
| 6,048,332 | A * | 4/2000 | Duffy et al. | 604/103.08 |
| 6,200,257 | B1 | 3/2001 | Winkler | |
| 6,210,392 | B1 | 4/2001 | Vigil et al. | |
| 6,544,223 | B1 | 4/2003 | Kokish | |
| 6,592,568 | B2 * | 7/2003 | Campbell | 604/509 |
| 6,663,590 | B2 * | 12/2003 | Blatter | 604/103.01 |
| 6,695,863 | B1 | 2/2004 | Ramzipoor et al. | |
| 6,733,474 | B2 | 5/2004 | Kusleika | |
| 6,740,104 | B1 | 5/2004 | Solar et al. | |
| 6,749,583 | B2 | 6/2004 | Briscoe et al. | |
| 6,951,555 | B1 | 10/2005 | Suresh et al. | |
| 2005/0124971 | A1 * | 6/2005 | Koch et al. | 604/509 |
| 2005/0288632 | A1 * | 12/2005 | Willard | 604/103.01 |
| 2006/0190022 | A1 * | 8/2006 | Beyar et al. | 606/192 |
| 2006/0206028 | A1 * | 9/2006 | Lee et al. | 600/471 |

OTHER PUBLICATIONS

International Preliminary Report on Patentability and Written Opinion, PCT/US2007/001691, Aug. 7, 2008.

\* cited by examiner

*Primary Examiner* — Nicholas D Lucchesi
*Assistant Examiner* — Nathan R Price
(74) *Attorney, Agent, or Firm* — Kenyon & Kenyon LLP

(57) ABSTRACT

The present application includes devices, systems and methods for therapeutic agent delivery. A device in accord with the invention may include a first infusion lumen having a proximal end, a distal end, a longitudinal axis and a therapeutic agent. This device may also include an inflatable balloon in fluid communication with the first infusion lumen, the inflatable balloon having an exit outlet wherein the device is configured to exert pressure at a target site with an external surface of the balloon, the exerted pressure greater than a target pressure prior to the therapeutic agent exiting the inflatable balloon. A method in accord with the invention may include positioning a delivery device near an intended treatment site, injecting therapeutic agent through an infusion lumen into an inflatable balloon, and determining a target pressure at a target site by monitoring the blood pressure of a patient.

22 Claims, 4 Drawing Sheets

FLOW-INFLATED DIFFUSION THERAPEUTIC DELIVERY

TECHNICAL FIELD

The present invention relates to the delivery of therapeutic agent to a target site of an organic vessel. More specifically, the invention regards devices, systems, and methods that employ a catheter or other device and inflatable membrane to deliver a therapeutic agent from the catheter to a target site, most often within the body of a patient.

BACKGROUND

Vasculature and muscle-related ailments, such as atherosclerosis and myocardial infarction, are common problems. Various procedures used to treat such ailments may employ a medical catheter having an inflatable balloon attached to a shaft, which is advanced through the vessel until the balloon is adjacent to the desired treatment site. The balloon is then inflated and medication released into the target treatment site. The balloon may serve to block flow of blood through the vessel, or to expand the vessel for ease of treatment. These devices utilize a guide wire, with the guide wire port often also serving as the infusion port to deliver a therapeutic agent. These devices also utilize small lumens with limited flow capabilities.

However, such procedures are not always successful in treating the ailment. As a result, a number of other devices have been suggested for use in conjunction with these procedures. Unfortunately, such devices may also not be entirely satisfactory. Specifically, a majority if not all of the therapeutic agent may not penetrate the vessel wall and may be washed away into the blood stream. Due to the toxic nature of some fluids, this procedure jeopardizes the health of the patient. Further, because the fluid is washed away, the treatment on the vessel is relatively ineffective. Some devices may block the flow of blood to the vessel in order to reduce these effects. However, it is desirable that the flow not be blocked for an extended period of time, to lessen the chance of injury to the patient. Current devices must accomplish occlusion of blood flow prior to delivery of a therapeutic agent, requiring flow within the vessel to be blocked for an extended period of time.

SUMMARY OF THE INVENTION

The present invention includes a device for and method of delivering therapeutic agent in a vessel, wherein the device occludes blood flow within the vessel during delivery of the therapeutic agent and can deliver therapeutic agent at a range of pressures, rates, and volumes.

A device for delivering a bolus of therapeutic agent is provided, wherein the device comprises a first infusion lumen and an inflatable balloon on a catheter, thorascope, endoscope, or other device. The balloon may be deflated and disposed within the infusion lumen until the device is positioned at the intended delivery site. The inflatable balloon is preferably inflatable with pressure created by a flow of therapeutic agent into the balloon. As the balloon inflates, it may occlude blood flow within a vessel. Once the balloon is inflated, or as it inflates, therapeutic agent is delivered to the target site. The inflatable balloon may comprise a porous material to allow the therapeutic agent to exit the interior of the balloon at a desired pressure. The occlusion of blood within the vessel and the rate at which therapeutic agent flows into and out of the balloon may result in the therapeutic agent being delivered at a pressure higher than the normal pressure of the target site. After delivery of the therapeutic agent, the balloon may be deflated and withdrawn into the infusion lumen, for example by applying a vacuum to the infusion lumen. When the balloon is deflated, the transverse diameter of the inflatable balloon may be, for example, not more than the diameter of the infusion lumen.

An inflatable balloon or other elastic membrane may be disposed at the distal end of a delivery device such as a catheter, endoscope, thorascope, or other similar device. The infusion lumen may comprise a flexible catheter or other similar device A device comprising an infusion lumen and inflatable balloon is provided, wherein the inflatable balloon may comprise at least one exit outlet. The exit outlet may comprise one or more openings in the balloon, or it may comprise a porous membrane. A filter may be disposed within the exit outlet to allow for filtering or straining of the therapeutic agent prior to delivery. For example, it may be desirable to strain a therapeutic agent comprising a mixture of a liquid and a solid prior to delivery at the intended target site. The filter may be comprised of a material different from the material comprising the balloon.

The device may further comprise a wire port. The wire port may be disposed along the longitudinal axis of the device, allowing a guide wire to be used to position the device at the desired treatment site. The device may be disposed at the distal end of the guide wire, or it may be disposed along the length of the guide wire to allow for different modes of operation.

The device may further comprise a second infusion lumen disposed parallel to the first infusion lumen. The second infusion lumen is also in fluid communication with the inflatable balloon, such that a therapeutic agent delivered through the second lumen may mix with a therapeutic agent delivered through the first lumen as the balloon inflates. The interior of the balloon may comprise a mixing region to facilitate mixing of separate therapeutic agents. Such a configuration may be advantageous when the operator desires to deliver multiple therapeutic agents, that require mixing immediately prior to delivery, to a single target site. The proximal end of a delivery means such as a catheter, thorascope, or endoscope, may comprise a means for delivering multiple therapeutic agents simultaneously. For example, a proportional dual lumen hub and syringe may be used.

The device may further comprise a micro-pump in fluid communication with the first infusion lumen. Such a configuration may be desirable to provide consistency in dose rates, amounts, and pressures, with limited operator interaction. In configurations having multiple infusion lumens, multiple micro-pumps may also be used such that each infusion lumen is in fluid communication with a micro-pump. There are numerous other embodiments of the invention as well.

DETAILED DESCRIPTION

Figure 1:
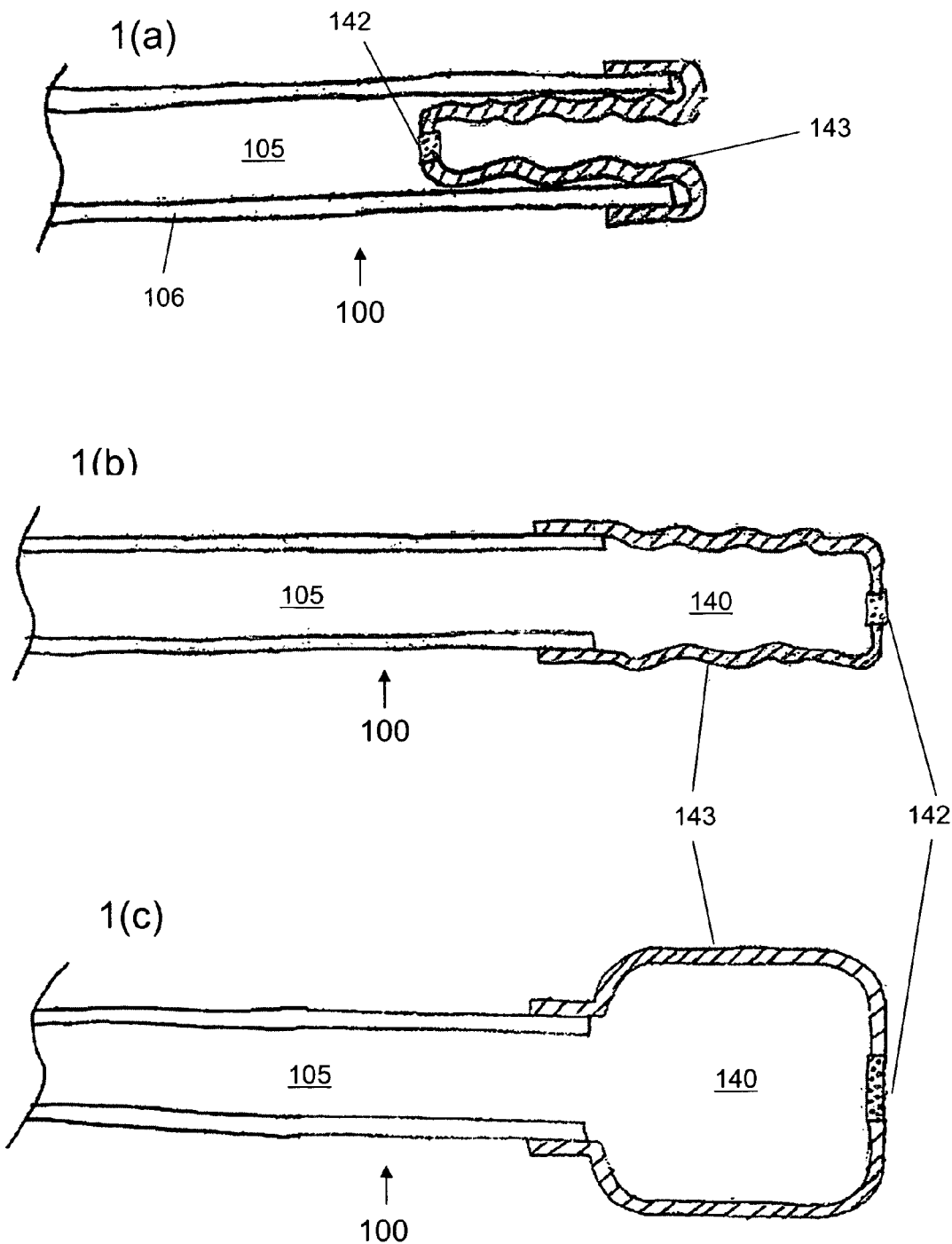
FIG. 1 shows enlarged side cut-away views of a catheter with balloon that can be inflated by a flow of therapeutic agent and retracted into the catheter in accord with the invention.

FIG. 1 shows the distal end of a delivery device 100 having a flow-inflatable balloon 140 that can be retracted into the catheter 106. Delivery device 100 may comprise infusion lumen 105 and inflatable balloon 140. Infusion lumen 105 may be defined by a flexible catheter 106, or it may be defined by other devices, including a thorascope, endoscope, or other delivery means. Infusion lumen 105 may be of various sizes, and may be capable of delivering a range of therapeutic volumes. Larger lumen size may be used, for example, in order to allow a larger quantity of therapeutic agent to be delivered in a short time. As shown in FIG. 1(a), prior to being positioned at or near the intended delivery site, balloon 140 may be in a deflated configuration. It may further be disposed within infusion lumen 105.

When a therapeutic agent is delivered through infusion lumen 105, pressure from the therapeutic agent may cause inflatable balloon 140 to inflate as shown in FIGS. 1(b) and 1(c). When balloon 140 is inflated to a desired size or pressure as shown in FIG. 1(c), therapeutic agent may be delivered to the intended delivery site. For example, balloon 140 may be inflated such that it occludes the flow of blood or other fluid within a target vessel, resulting in a pressure higher than the normal pressure of the intended delivery site.

The "normal pressure" of or at an intended delivery site refers to the pressure existing prior to inflation of the inflatable balloon. It may similarly refer to the maximum pressure that normally occurs at the target delivery site. For example, when the target delivery site is within a blood vessel, the blood flow within the vessel may be occluded such that the therapeutic agent is delivered at a pressure higher than the systolic pressure within the vessel. Such pressure then drives the therapeutic agent being delivered into the capillary bed. Similarly, higher pressures can be used to limit retrograde flow of the therapeutic agent during delivery.

Balloon 140 may occlude blood flow at or near the intended delivery site for short and prolonged periods of time. Since balloon 140 is inflated with the flow of therapeutic agent, it may inflate and occlude blood flow as the therapeutic agent is being delivered, thereby removing the need for a separate process to inflate the balloon in order to occlude the vessel. Thus, the time that the vessel must be occluded to obtain successful delivery of a therapeutic agent is reduced. However, as explained herein, embodiments of the present invention may include multiple lumens, some of which may be used to transport therapeutic and some of which may be used to transport other substances.

Balloon 140 may comprise a porous material 143. A "porous material" refers to a material that allows the passage of a fluid under certain conditions, but prevents flow under other conditions. A "porous material" may also refer to a material that limits the rate of flow of a substance across a barrier without preventing such flow. For example, porous material 143 may allow therapeutic agent to exit balloon 140 when the pressure created by delivery of the therapeutic agent into balloon 140 exceeds or meets a specific or minimum pressure. One such target pressure may be the systolic or diastolic pressure of the patient upon which the device is being used. Such a configuration may be used to, for example, control the rate at which the therapeutic agent is delivered to the intended delivery site.

Balloon 140 may comprise exit outlet 142, which may further comprise one or more openings in the casing of balloon 140. Different placements of such openings may allow for a variety of delivery configurations. Exit outlet 142 may further comprise a filter. A filter may be used to allow for the therapeutic agent being delivered to be strained prior to delivery at the target delivery site. This may be advantageous, for example, when the therapeutic agent comprises a mix of solid and liquid materials, only portions of which are to be delivered to the target site. It may similarly be advantageous when the therapeutic agent comprises a mix of multiple substances which are to be mixed prior to delivery at the desired target site. For example, the filter may strain clumps of solid material from the therapeutic agent and prevent such material from being delivered to the target site. Similarly, the filter may restrict the flow of therapeutic agent in general, thus controlling the rate at which therapeutic agent is released from the balloon and affecting the pressure and rate of change of pressure within the balloon.

After delivery of the therapeutic agent to the target site, balloon 140 may be returned to its initial configuration, shown in FIG. 1(a), for example, by applying a vacuum to infusion lumen 105. Balloon 140 may also return to its initial configuration once the internal pressure of the device is reduced, for example, when the therapeutic agent is no longer flowing through infusion lumen 105 and balloon 140. In such configurations, balloon 140 may comprise a shape-memory material such as Nitinol or other similar material. A shape-memory material allows an object to return to its initial shape, by exposure to external conditions, after being deformed to a different shape. Thus, balloon 140 may comprise a shape-memory material, with the initial shape of balloon 140 being that shown in FIG. 1(a). As the internal pressure is increased, balloon 140 then deforms to a shape such as that shown in FIG. 1(c); that is, to an inflated configuration. Once therapeutic agent is no longer flowing from infusion lumen 105 through balloon 140, balloon 140 may return to its original, "memory" shape shown in FIG. 1(a).

Figure 2:
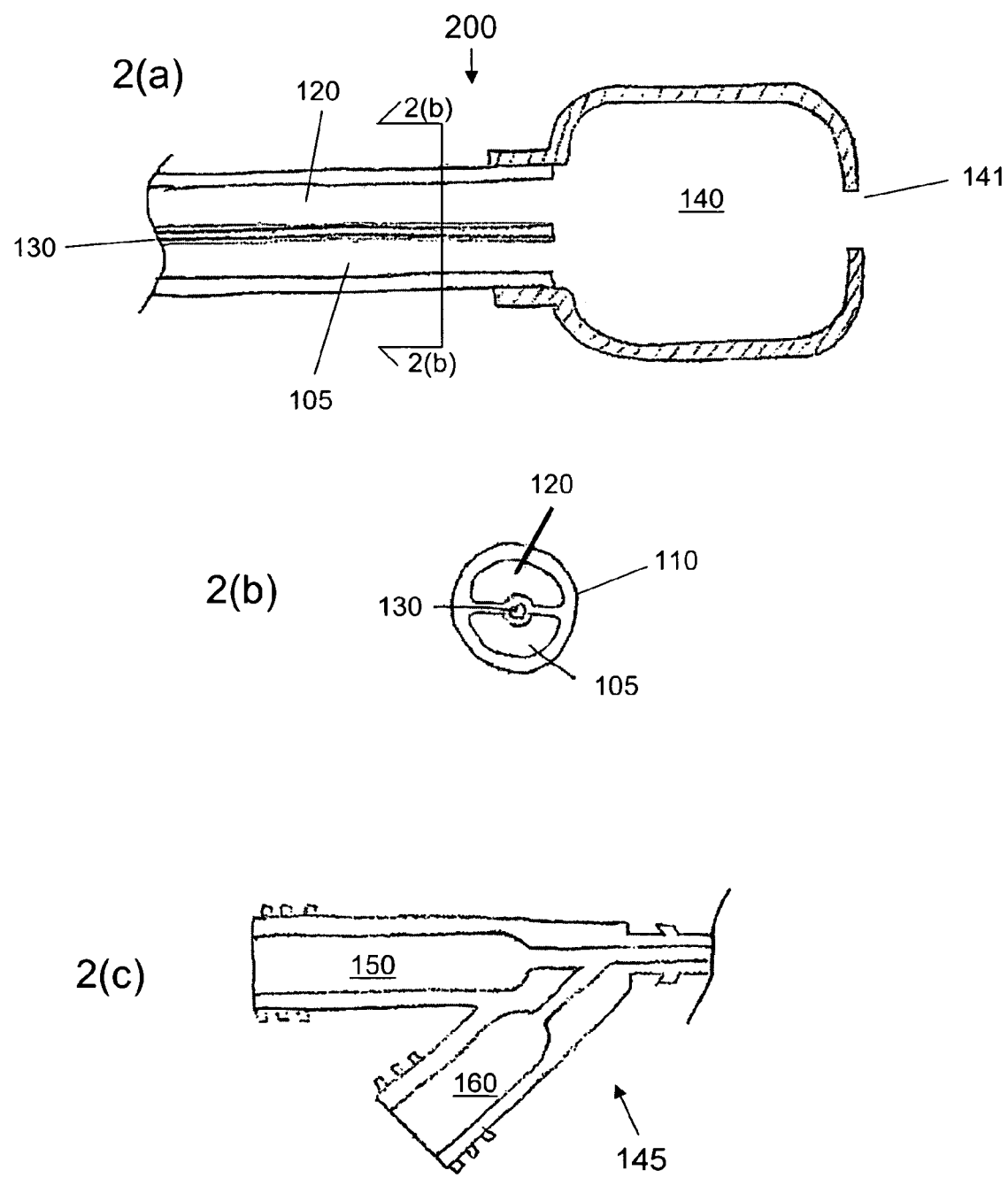
FIG. 2 shows enlarged side and end views of components of a device having a catheter with multiple infusion lumens and a flow-inflatable balloon, and an injection hub having a guide wire port and an injection port in accord with the invention.

FIG. 2 shows a delivery device having multiple infusion lumens in accord with the present invention. Referring to FIG. 2(a), delivery device 200 comprises a first infusion lumen 105 and inflatable balloon 140 as described above. Delivery device 200 may also comprise a second infusion lumen 120. Therapeutic agent may be delivered to balloon 140 through infusion lumens 105, 120, or both. Infusion lumens 105 and 120 may provide different therapeutic agents, or subcomponents of a single therapeutic agent that may be mixed prior to delivery at the intended site. When one or more therapeutic agents are delivered to balloon 140, pressure causes balloon 140 to inflate as described above. If multiple therapeutic agents are used, balloon 140 may further comprise a mixing region, or the interior of balloon 140 may serve as a mixing region, such that multiple substances delivered via infusion lumens 105 and 120 may mix prior to delivery at the intended delivery site. For example, infusion lumen 105 may deliver a first therapeutic agent to balloon 140, and infusion lumen 120 may deliver a second therapeutic agent to 105. The first and second therapeutic agents mix within balloon 140, and are then delivered to the intended treatment site. Balloon 140 may further comprise an exit outlet 141 as described above. Exit outlet 141 may further comprise a filter (not shown) as previously described. A filter may be used when multiple substances are delivered via infusion lumens 105 and 120. For example, if two substances are delivered via infusion lumens 105 and 120, the mixture may result in solid material which is not part of the desired therapeutic agent to be delivered. A filter is then used to remove the unwanted solid material from the therapeutic agent prior to delivery at the intended site.

Delivery device 200 may further comprise a wire port 130. Wire port 130 is disposed along or parallel to the longitudinal axis of the delivery device. A guide wire (not shown) may be inserted through wire port 130 to allow for controlled placement of the delivery device at a desired treatment site.

FIG. 2(b) shows an enlarged cross-section of a portion of the delivery device taken along line 2(b) of FIG. 2(a). Infusion lumens 105 and 120, and wire lumen 130, previously described, are shown. Wire lumen 130 may be disposed between infusion lumens 105 and 120. Infusion lumens 105 and 120 and wire lumen 130 may be disposed within a catheter 110 or other delivery means. Wire lumen 130 may be disposed along the longitudinal axis of catheter 110. Different configurations of the invention may be possible. For example, delivery device 200 may be configured and operated as a single operator exchange device. Similarly, it may be configured and operated in a monorail configuration. Other configurations and operating means may be possible.

Referring to FIG. 2(c), a dual port hub 145 is shown. Dual port hub 145 may be disposed at the proximal end of a delivery means such as catheter 110 shown in FIG. 2(b). An operator may insert a guide wire (not shown) into guide wire port 150, which may be connected to wire lumen 130 as shown in FIGS. 2(a) and 2(b). Similarly, infusion port 160 may be in fluid communication with infusion lumen 105, and may be used to deliver a therapeutic agent to infusion lumen 105. Other types of hubs and arrangements of ports are possible in accord with the present invention.

FIGS. 3(a)-(c) show components of a delivery device in accord with the invention. Delivery device 300 is disposed along guide wire 131, where guide wire 131 is parallel with the longitudinal axis of delivery device 300 and passes through wire lumen 130. Delivery device 300 may be disposed at or near the distal end of guide wire 131, or it may be disposed at a point on the length of guide wire 131. Delivery device 300 comprises infusion ports 105 and 120 in fluid communication with balloon 140 as described above. As shown, wire lumen 130 is disposed parallel to infusion lumens 105 and 120, and inflatable balloon 140 is disposed at the distal end of infusion ports 105 and 120. Other configurations are possible, and may be determined based on, for example, the mode of operation desired or the location of the target site within a patient's body.

Inflatable balloon 140 in FIG. 3(a) may comprise a variety of means for delivering therapeutic agents. For example, exit outlet 141 may comprise one or more openings in balloon 140. Filter 142 may be disposed in exit outlet 141. Balloon 140 may comprise a porous material 143, to allow diffusion of therapeutic agents to the outside of balloon 140.

In use, after delivery device 300 has been positioned at or near the intended delivery site, a therapeutic agent may be delivered to infusion lumens 105 and 120. A single therapeutic agent may be used, or a different therapeutic agent may be delivered via each infusion lumen as previously described. Therapeutic agents may mix in balloon 140 prior to being delivered to the intended delivery site.

Figure 3:
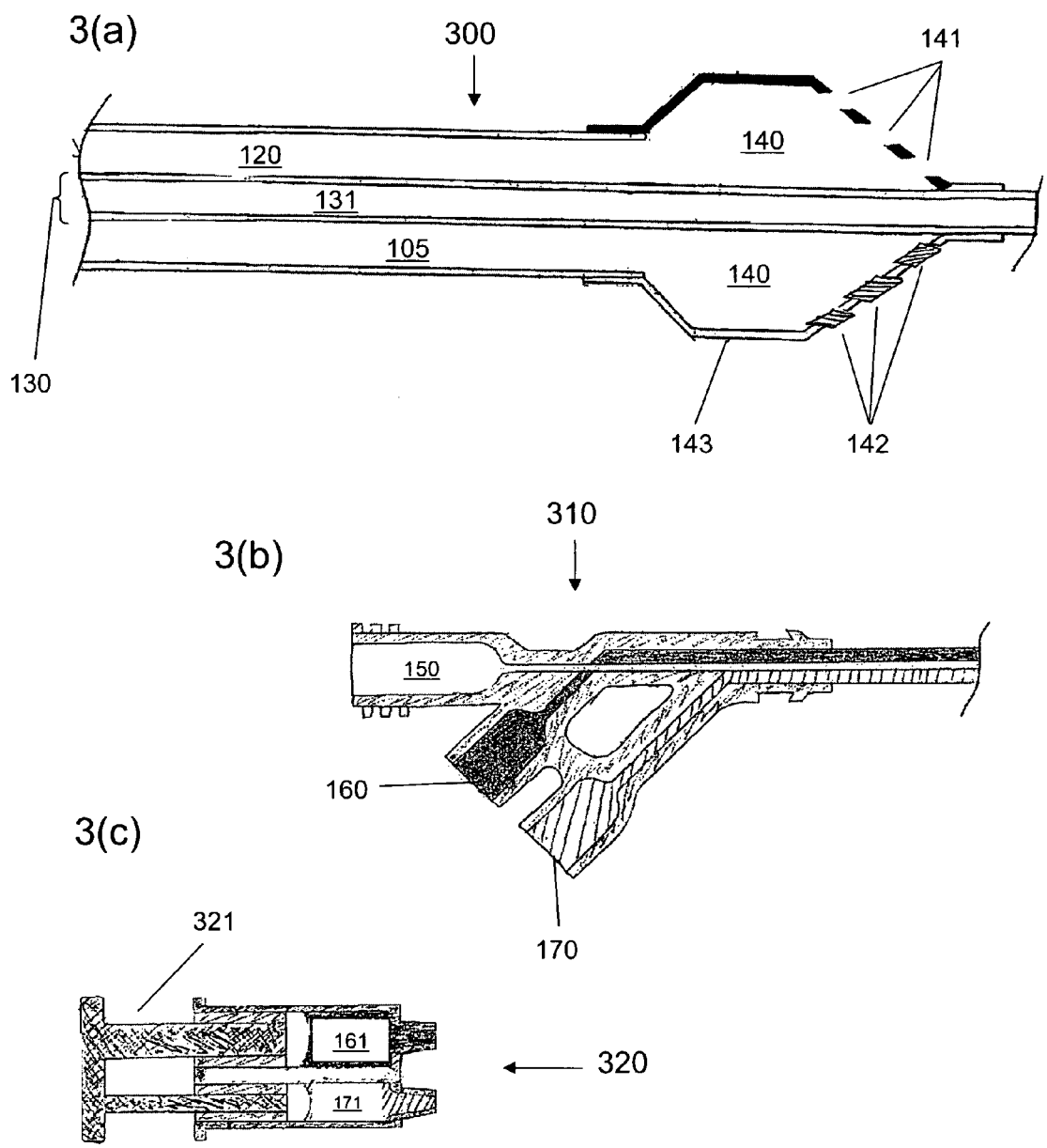
FIG. 3 shows an enlarged side cut-away view of components of a device having multiple infusion lumens, a wire lumen, a flow-inflatable balloon, an injection hub, and a dual lumen syringe in accord with the invention.

As shown in the device of FIG. 3, some embodiments of the present invention may provide a dual port hub 310 and dual lumen syringe 320. Dual port hub 310 may be disposed at the proximal end of a means, such as a catheter, for positioning delivery device 300 at an intended delivery site. A guide wire 131 may be inserted into wire port 150. Wire port 150 may be connected to wire lumen 130, such that a guide wire may be disposed contiguously within both wire port 150 and wire lumen 130. Infusion ports 160 and 170 may be in fluid communication with, for example, infusion lumens 120 and 105, respectively, to allow therapeutic agents to be delivered to infusion ports 160 and 170. A single therapeutic agent may be used, or a different therapeutic agent or component of a therapeutic agent may be delivered to each of infusion ports 160 and 170. Therapeutic agents may be delivered from infusion ports 160 and 170 to infusion lumens 120 and 105, for example, by increased pressure at the proximal end of infusion ports 160 and 170. For example, dual lumen syringe 320 can provide pressure to a therapeutic agent placed in syringe chambers 161 and 171, causing the therapeutic agent to flow through infusion ports 160 and 170 into infusion lumens 120 and 105, respectively. Dual lumen syringe 320 may be disposed adjacent to dual port hub 310, such that syringe chambers 161 and 171 are in fluid communication with infusion ports 160 and 170, respectively. When dual lumen plunger 321 is closed, therapeutic agents may be delivered from syringe chambers 161 and 171 to infusion ports 160 and 170, respectively. Syringe chambers 161 and 171 may be different sizes, or different amounts of therapeutic agent may be inserted into each for delivery to infusion lumens 120 and 105. Such a configuration may be used to deliver different quantities of therapeutic agents to infusion lumens 105 and 120, allowing for multiple therapeutic agents to be mixed in balloon 140 in known ratios prior to delivery to the intended delivery site.

Figure 4:
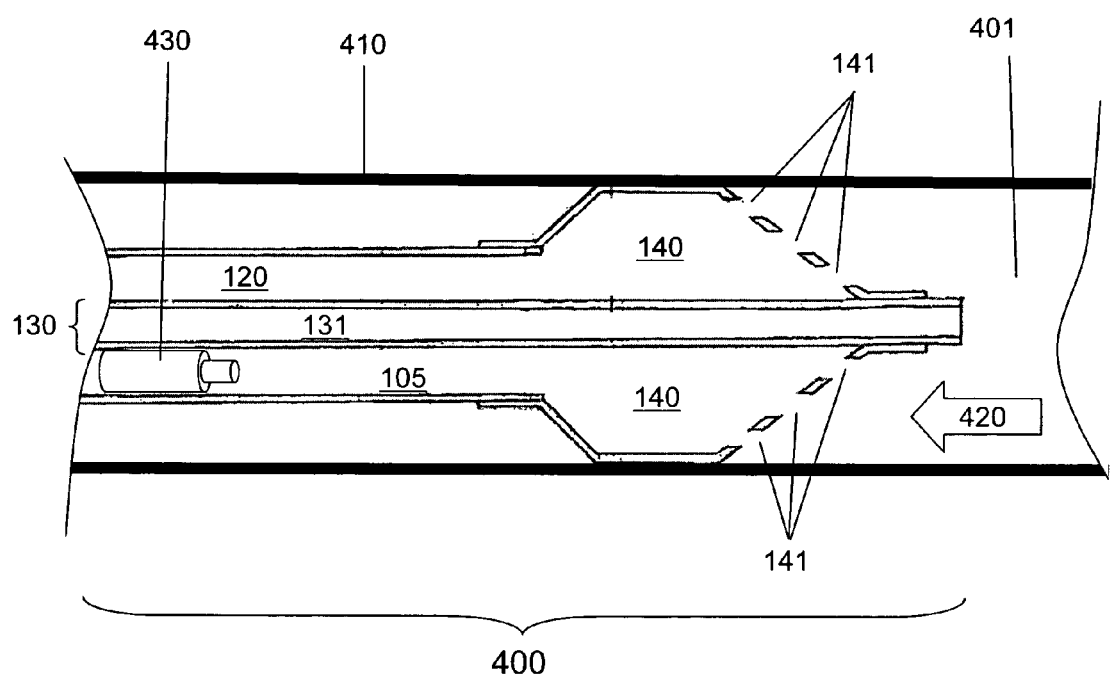
FIG. 4 shows an enlarged side view of the distal end of a delivery system with a micro-pump positioned at a target site within a vessel in accord with the invention.

FIG. 4 shows the distal end of a delivery system positioned near a target site of a patient to be treated. Vessel 410 may be, for example, a blood vessel with desired treatment site 401. Delivery device 400 may be delivered to or near desired treatment site 401 using guide wire 131. It may be deployed in a retrograde manner, such that therapeutic agent will flow in the opposite direction of blood flow 420 when it is delivered. Once delivery device 400 is disposed at or near the desired treatment site 401, balloon 140 is inflated by delivering a therapeutic agent or therapeutic agents into balloon 140 via infusion lumens 105, infusion lumen 120, or both, as previously discussed. Balloon 140 may inflate to a size sufficient to occlude blood flow through vessel 410. Once balloon 140 is inflated, therapeutic agent may exit balloon 140 via exit outlet 141. Balloon 140 is in fluid communication with the interior of vessel 410, and especially with desired treatment region 401. Fluid pressure within balloon 140 may be sufficiently high to deliver therapeutic agent to desired treatment region 401. In some uses, balloon 140 is inflated to a pressure higher than the systolic pressure within vessel 410, which may aid infusion of therapeutic agent into the capillary bed and prevent retrograde flow of therapeutic agent into the device.

Delivery device 400 may further comprise one or more micro-pumps, such as micro-pump 430, which may be in fluid communication with one or more of infusion lumens 120 and 105. Micro-pump 430 may be disposed within infusion lumen 105, and electrically connected to a control unit (not shown) on the exterior of the device. The control unit may be part of a hub, such as dual port hub 310 in FIG. 3. An operator may manipulate the control unit in order to utilize micro-pump 430. Use of one or more micro-pumps may be used to aid an operator in delivering a consistent volume of therapeutic agent at a consistent pressure between treatments. Such a configuration reduces variance due to human operation of the device, or variance that may occur between different operators.

As used herein and as will be understood by one of skill in the art, the "proximal" end of a device or portion of a device refers to the end closest to the operator of the device. Similarly, the "distal" end of a device or portion of a device refers to the end farthest from the operator of the device.

The term "therapeutic agent" as used throughout includes one or more "therapeutic drugs" or "genetic material." The term "therapeutic agent" used herein includes pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences. The therapeutics administered in accordance with the invention includes the therapeutic agent(s) and solutions thereof.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such as heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl) ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; angiotensin converting enzyme (ACE) inhibitors; beta-blockers; bAR kinase (bARKct) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins ("MCP-1) and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds having a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative ($Lin^-$) cells including $Lin^-CD34^-$, $Lin^-CD34^{30}$, $Lin^-cKit^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, $G_0$ cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polystyrene; polyisobutylene copolymers, styrene-isobutylene block copolymers such as styrene-isobutylene- styrene tri-block copolymers (SIBS)

and other block copolymers such as styrene-ethylene/butylene-styrene (SEBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by various methods including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

The examples described and illustrated herein are merely illustrative, as numerous other embodiments may be implemented without departing from the spirit and scope of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A device for delivering therapeutic agent to a target site in a vessel having a vessel wall and a vessel interior, the device comprising:
    a first infusion lumen having a proximal end, a distal end, and a longitudinal axis, the first infusion lumen containing a therapeutic agent;
    a second infusion lumen having a proximal end, a distal end, and a longitudinal axis, the second infusion lumen containing a substance for mixing with the therapeutic agent; and
    an inflatable balloon disposed at the distal ends of the first and second infusion lumens and in fluid communication with the first and second infusion lumens, the balloon having a proximal end, a distal end and an intermediate surface between the proximal end and distal end, the intermediate surface configured to contact the vessel wall, the inflatable balloon being the only balloon in fluid communication with the first and second infusion lumens, the inflatable balloon having an exit outlet in only the distal end of the balloon;
    wherein the device is configured to exert pressure, such that when the exerted pressure is greater than a target pressure the therapeutic agent exits the inflatable balloon through the exit outlet into the vessel interior.

2. The device of claim 1, wherein the device comprises a single balloon.

3. The device of claim 1, wherein the diameter of the inflatable balloon is not more than the diameter of the first infusion lumen when the inflatable balloon is deflated, so that the balloon may be deflated and withdrawn into the infusion lumen.

4. The device of claim 1, wherein the device is configured so as to develop a therapeutic agent pressure within the inflatable balloon greater than the target pressure.

5. The device of claim 4, wherein the exit outlet is sized to release the therapeutic agent within the balloon after the therapeutic agent within the balloon reaches a target pressure.

6. The device of claim 1, wherein the inflatable balloon comprises a porous material.

7. The device of claim 1, wherein the balloon further comprises a filter.

8. The device of claim 7, wherein the filter is comprised of a material different than a material comprising the balloon.

9. The device of claim 7, wherein the filter is disposed within the exit outlet and wherein the filter is configured to restrict the flow of therapeutic agent through the exit outlet.

10. The device of claim 1, further comprising a micropump in fluid communication with the first infusion lumen.

11. The device of claim 1, wherein the second infusion lumen is in fluid communication with the first infusion lumen.

12. The device of claim 1, further comprising a means for positioning the device at the target site.

13. The device of claim 12, wherein the proximal end of the first infusion lumen is disposed at the distal end of the means for positioning the device.

14. The device of claim 1, wherein the inflatable balloon may be retracted into the first infusion lumen.

15. The device of claim 1, wherein the exit outlet further comprises a filter.

16. The device of claim 1, further comprising a wire port disposed along the longitudinal axis of the first infusion lumen.

17. The device of claim 1, wherein the inflatable balloon further comprises a mixing region.

18. The device of claim 1, wherein the first infusion lumen and the exit outlet are configured to develop a therapeutic agent pressure within the inflatable balloon greater than the target pressure.

19. A device to deliver a therapeutic agent, comprising:
- a guide wire having a proximal end, a distal end, and a longitudinal axis;
- a first infusion lumen having a proximal end, a distal end, and a longitudinal axis;
- a second infusion lumen having a proximal end, a distal end, and a longitudinal axis; and
- an inflatable balloon is disposed at the distal ends of the infusion lumens, the inflatable balloon being the only balloon in fluid communication with the first and second infusion lumens, wherein the balloon has a proximal end, a distal end and an intermediate surface between the proximal end and distal end, and wherein the longitudinal axis of the inflatable balloon is parallel to the longitudinal axes of the infusion lumens;
- wherein the guide wire is disposed parallel to the longitudinal axes of the infusion lumens; and
- wherein the balloon contains an exit outlet in only the distal end of the balloon, the exit outlet configured to restrict flow of therapeutic agent from the balloon and also configured to retard the release of therapeutic agent from the balloon until therapeutic agent pressure within the balloon reaches a target pressure.

20. The device of claim 19, wherein the balloon contains a plurality of exit outlets.

21. The device of claim 19, wherein the target pressure is determined by measuring the blood pressure of a patient prior to delivering the therapeutic agent with the device.

22. A method of delivering a therapeutic agent within a vessel having a vessel wall and a vessel interior, the method comprising the steps of:
- positioning a delivery device having a first infusion lumen, a second infusion lumen, an inflatable balloon, a proximal end, a distal end, and a longitudinal axis near an intended treatment site in the vessel, the inflatable balloon being the only balloon in fluid communication with the first and second infusion lumens, the balloon having a proximal end, a distal end and an intermediate surface between the proximal end and distal end, the intermediate surface configured to contact the vessel wall, the balloon having an exit outlet in only the distal end of the balloon;
- injecting the therapeutic agent through the first infusion lumen into the inflatable balloon, wherein the therapeutic agent causes the inflatable balloon to inflate to a target pressure;
- injecting a substance through the second infusion lumen for mixing with the therapeutic agent;
- determining a target pressure at a target site by monitoring the blood pressure of a patient; and
- delivering the therapeutic agent through the exit outlet into the interior of the vessel when a pressure inside the balloon exceeds the target pressure.

* * * * *